(12) United States Patent  (10) Patent No.: US 7,312,179 B2
Ehrenfreund et al.  (45) Date of Patent: Dec. 25, 2007

(54) CYCLOPROPYL-THIENYL-CARBOXAMIDE AS FUNGICIDES

(75) Inventors: Josef Ehrenfreund, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/532,847

(22) PCT Filed: Oct. 24, 2003

(86) PCT No.: PCT/EP03/11805

§ 371 (c)(1), (2), (4) Date: Apr. 27, 2005

(87) PCT Pub. No.: WO2004/039799

PCT Pub. Date: May 13, 2004

(65) Prior Publication Data

US 2006/0030567 A1    Feb. 9, 2006

(30) Foreign Application Priority Data

Nov. 1, 2002   (GB) ................... 0225554.5

(51) Int. Cl.
  *A01N 43/36*   (2006.01)
  *C07D 409/00*  (2006.01)
(52) U.S. Cl. ..................... 504/207; 548/527
(58) Field of Classification Search ................ 504/287; 548/527
  See application file for complete search history.

(56) References Cited

U.S. PATENT DOCUMENTS 4,156,009 A * 5/1979 Cognacq ............ 514/221
6,699,818 B1 * 3/2004 Walter et al. .......... 504/287

FOREIGN PATENT DOCUMENTS

| EP | 0253502  | 1/1988 |
| EP | 0737682  | 10/1996 |
| GB | 2126587  | 3/1984 |
| WO | 03074491 | 9/2003 |

* cited by examiner

*Primary Examiner*—Sabiha N. Qazi
(74) *Attorney, Agent, or Firm*—Rebecca A. Howard

(57) ABSTRACT

A fungicidally active compound of formula (I): where X is (X1), (X2) or (X3); Het is a 5- or 6-membered heterocyclic ring containing one to three heteroatoms, each independently selected from oxygen, nitrogen and sulphur, provided that the ring is not 1,2,3-triazole, the ring being substituted by groups $R^4$, $R^5$ and $R^6$; $R^1$ and $R^2$ are each, independently, hydrogen, halo or methyl; R3 is optionally substituted $C_{2-12}$ alkyl, optionally substituted $C_{2-12}$ alkenyl, optionally substituted $C_{2-12}$ alkynyl, optionally substituted $C_3^{-12}$ cycloalkyl, optionally substituted phenyl or optionally substituted heterocyclyl; $R^4$, $R^5$ and $R^6$ are each, independently, selected from hydrogen, halo, cyano, nitro, $C_{1-4}$ alkyl, $C_{1-4}$ haloalkyl, $C_{1-4}$ alkoxy($C_{1-4}$)alkylene and $C_{1-4}$ haloalkoxy ($C_{1-4}$)alkylene, provided that at least one of $R^4$, $R^5$ and $R^6$ is not hydrogen; and $R^7$ and $R^8$ are each, independently, hydrogen, halogen, $C_{1-4}$ alkyl or Clue haloalkyl; the invention also relates to the preparation of these compounds, to novel intermediates used in the preparation of these compounds, to the preparation of intermediates, to agrochemical compositions which comprise at least one of the novel compounds as active ingredient and to the use of the active ingredients or compositions in agriculture or horticulture for controlling or preventing infestation of plants by phytopathogenic microorganisms, preferably fungi

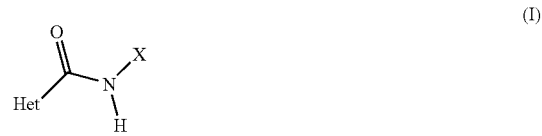
(I)

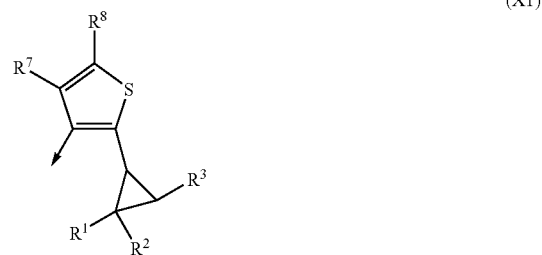

(X1)

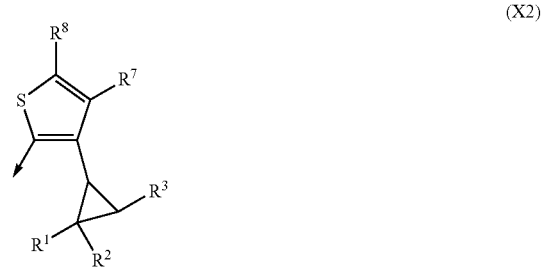

(X2)

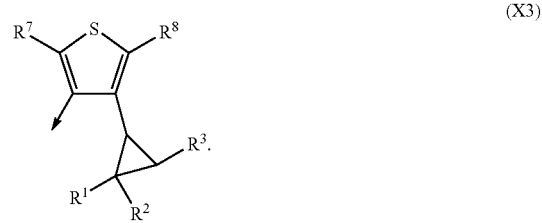

(X3)

9 Claims, No Drawings

CYCLOPROPYL-THIENYL-CARBOXAMIDE AS FUNGICIDES

This application is a 371 of International Application No. PCT/EP03/011805 filed Oct. 24, 2003, which claims priority to GB 0225554.5 filed Nov. 1, 2002, the contents of which are incorporated herein by reference.

The present invention relates to novel ortho-cyclopropyl-thienyl-carboxamides which have microbiocidal activity, in particular fungicidal activity. The invention also relates to the preparation of these compounds, to novel intermediates used in the preparation of these compounds, to the preparation of intermediates, to agrochemical compositions which comprise at least one of the novel compounds as active ingredient and to the use of the active ingredients or compositions in agriculture or horticulture for controlling or preventing infestation of plants by phytopathogenic microorganisms, preferably fingi.

Fungicidal heterocyclic aromatic amides are disclosed in WO01/05769 A2, EP-A-0-737-682 and GB-A-2-126-587. Fungicidal tertiary amine compounds containing a cyclopropane ring are disclosed in EP-A-0-253-502.

The present invention provides a compound of formula (I):

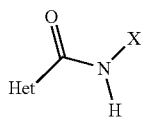

(I)

where X is (X1), (X2) or X(3);

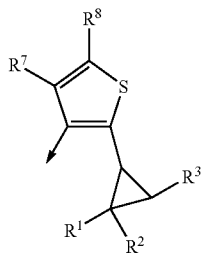

(X1)

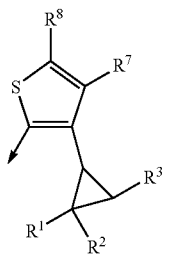

(X2)

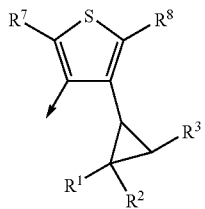

(X3)

Het is a 5- or 6-membered heterocyclic ring containing one to three heteroatoms, each independently selected from oxygen, nitrogen and sulphur, provided that the ring is not 1,2,3-triazole, the ring being substituted by groups $R^4$, $R^5$ and $R^6$; $R^1$ and $R^2$ are each, independently, hydrogen, halo or methyl; $R^3$ is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl; $R^4$, $R^5$ and $R^6$ are each, independently, selected from hydrogen, halo, cyano, nitro, $C_{1-4}$ alkyl, $C_{1-4}$ haloalkyl, $C_{1-4}$ alkoxy$(C_{1-4})$alkylene and $C_{1-4}$ haloalkoxy$(C_{1-4})$alkylene, provided that at least one of $R^4$, $R^5$ and $R^6$ is not hydrogen; and $R^7$ and $R^8$ are each, independently, hydrogen, halogen, $C_{1-4}$ alkyl or $C_{1-4}$ haloalkyl.

In another definition the present invention provides a compound of formula (I*):

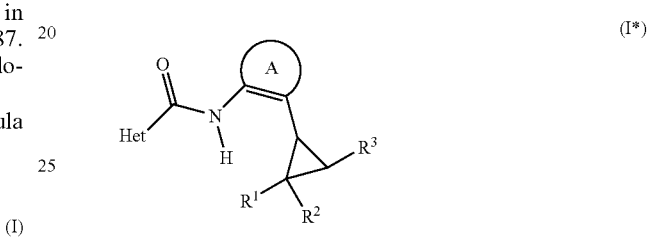

(I*)

where Het is a 5- or 6-membered heterocyclic ring containing one to three heteroatoms, each independently selected from oxygen, nitrogen and sulphur, provided that the ring is not 1,2,3-triazole, the ring being substituted by groups $R^4$, $R^5$ and $R^6$; A is a thienyl ring (selected from all possible thienyl isomers) being substituted by groups $R^7$ and $R^8$; $R^1$ and $R^2$ are each, independently, hydrogen, halo or methyl; $R^3$ is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl; $R^4$, $R^5$ and $R^6$ are each, independently, selected from hydrogen, halo, cyano, nitro, $C_{1-4}$ alky, $C_{1-4}$ haloalkyl, $C_{1-4}$ alkoxy$(C_{1-4})$alkylene and $C_{1-4}$ haloalkoxy$(C_{1-4})$alkylene, provided that at least one of $R^4$, $R^5$ and $R^6$ is not hydrogen; and $R^7$ and $R^8$ are each, independently, hydrogen, halogen, $C_{1-4}$ alkyl or $C_{1-4}$ haloalkyl.

Halo is fluoro, chloro or bromo.

Each alkyl moiety is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. Likewise, each alkylene moiety is a straight or branched chain.

When present, each optional substituent on an alkyl moiety is, independently, selected from halo, hydroxy, cyano, $COOC_{1-4}$alkyl, formyl, nitro, $C_{1-4}$alkoxy, $C_{1-4}$ haloalkoxy, $C_{1-4}$ alkylthio, $C_{1-4}$ haloalkylthio, HC(OR')=N and R'R"NN=C(H); where R' and R" are each, independently, hydrogen or $C_{1-4}$ alkyl Alkenyl and alkynyl moieties may be in the form of straight or branched chains. The alkenyl moieties, where appropriate, may be of either the (E-) or (Z-)-configuration. Examples are vinyl, alkyl and propargyl.

When present, each optional substituent on alkenyl or on alkynyl is, independently, selected from those optional substituents given above for an alkyl moiety.

Cycloalkyl includes cyclopropyl, cyclobutyl, cyclopentyl and cyclohexyl.

When present, each optional substituent on cycloalkyl is, independently, selected from $C_{1-3}$ alkyl and those optional substituents given above for an alkyl moiety.

The term heterocyclyl refers to a non-aromatic or aromatic ring containing up to 10 atoms including one or more (preferably one or two) heteroatoms, each independently, from O, S and N. Examples of such rings include 1,3-dioxolanyl, tetrahydrofuranyl, morpholinyl, thienyl and furyl.

When present, each optional substituent on phenyl or on heterocyclyl is, independently, selected from $C_{1-6}$ alkyl and those optional substituents given above for an alkyl moiety. When present, there are up to four optional substituents on phenyl, each independently selected.

It is preferred that, when present, each optional substituent on an alkyl moiety is, independently, selected from halo, hydroxy, methoxy, trifluoromethoxy, difluoromethoxy, cyano and nitro.

It is preferred that, when present, each optional substituent on alkenyl or on alkynyl is, independently, selected from halo and cyano.

It is preferred that, when present, each optional substituent on cycloalkyl is, independently, selected from methyl, ethyl, trifluoromethyl, methoxy, trifluoromethoxy and cyano.

It is preferred that, when present, each optional substituent on phenyl or on a heterocyclyl group is, independently, selected from halo, hydroxy, methoxy, trifluoromethoxy, difluoromethoxy and cyano.

It is preferred that Het is pyrrolyl, pyrazolyl, thiazolyl, pyridinyl, pyrimidinyl, thienyl, furyl, isothiazolyl or isoxazolyl (more preferably pyrrolyl, pyrazolyl or thiazolyl), each being substituted by groups $R^4$, $R^5$ and $R^6$.

Preferably $R^1$ and $R^2$ are, independently, hydrogen or fluoro.

Preferably $R^3$ is $C_{2-6}$ alkyl, optionally substituted $C_{3-8}$ cycloalkyl, phenyl, thienyl or furyl.

Preferably $R^4$, $R^5$ and $R^6$ are, independently, selected from hydrogen, halogen, $C_{1-4}$ alkyl, $C_{1-4}$ haloalkyl and $C_{1-4}$ alkoxy($C_{1-4}$)alkylene, provided that at least one of $R^4$, $R^5$ and $R^6$ is not hydrogen. More preferably $R^4$, $R^5$ and $R^6$ are, independently, selected from hydrogen, halogen, methyl, $C_{1-2}$ haloalkyl and methoxymethylene, provided that at least one of $R^4$, $R^5$ and $R^6$ is not hydrogen.

Preferably $R^7$ and $R^8$ are, independently, selected from hydrogen, halogen and methyl.

Compounds of formula (II):

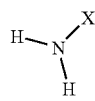

(II)

where X and $R^3$ are as defined above for a compound of formula (I); and $R^1$, $R^2$, $R^7$ and $R^8$ are each hydrogen, are also novel and are useful as intermediates in the preparation of compounds of formula (I).

Therefore in an alternative aspect, the present invention provides a compound of formula (II) where X and $R^3$ are as defined above for a compound of formula (I); and $R^1$, $R^2$, $R^7$ and $R^8$ are each hydrogen.

In an alternative definition, the present invention provides a compound of formula (II*),

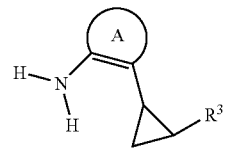

(II*)

where A is an unsubstituted thienyl ring (selected from all possible thienyl isomers) and $R^3$ is as defined above for a compound of formula (I).

The compounds of formulae (I), (II), (I*) and (II*) may exist as different geometric or optical isomers or in different tautomeric forms. For each formula, this invention covers all such isomers and tautomers and mixtures thereof in all proportions as well as isotopic forms such as deuterated compounds.

The compounds in Tables 1 to 18 below illustrate compounds of the invention.

Table V represents Table 1 (when V is 1), Table 2 (when V is 2) and represents Table 3 (when V is 3).

Table W represents Table 4 (when W is 4), represents Table 5 (when W is 5), represents Table 6 (when W is 6), represents Table 7 (when W is 7), represents Table 8 (when W is 8) and represents Table 9 (when W is 9).

Table X represents Table 10 (when X is 10), represents Table 11 (when X is 11) and represents Table 12 (when X is 12).

Table Y represents Table 13 (when Y is 13), represents Table 14 (when Y is 14) and represents Table 15 (when Y is 15).

Table Z represents Table 16 (when Z is 16), represents Table 17 (when Z is 17) and represents Table 18 (when Z is 18).

TABLE V

| Compound Number | $R^3$ |
|---|---|
| V.1 | $CH_2CH_3$ |
| V.2 | $CH_2CH_2CH_3$ |
| V.3 | $CH(CH_3)_2$ |
| V.4 | $CH_2CH_2CH_2CH_3$ |
| V.5 | $CH_2CH(CH_3)_2$ |
| V.6 | $C(CH_3)_3$ |
| V.7 | $CH_2CH_2CH_2CH_2CH_3$ |
| V.8 | $CH_2CH_2CH(CH_3)_2$ |
| V.9 | $CH_2CH_2CH(CH_3)_2$ |
| V.10 | cyclopropyl |
| V.11 | cyclobutyl |
| V.12 | cyclopentyl |
| V.13 | cyclohexyl |
| V.14 | cycloheptyl |
| V.15 | cyclooctyl |
| V.16 | phenyl |
| V.17 | 4-Cl—$C_6H_4$ |
| V.18 | 4-F—$C_6H_4$ |
| V.19 | 4-Br—$C_6H_4$ |
| V.20 | 2-thienyl |
| V.21 | 3-thienyl |
| V.22 | 2-furyl |
| V.23 | 3-furyl |
| V.24 | α-methylcyclopropyl |

TABLE W

| Compound Number | R¹ | R² | R³ | R⁴ | R⁵ | R⁶ |
|---|---|---|---|---|---|---|
| W.1 | H | H | CH$_2$CH$_3$ | CF$_3$ | CH$_3$ | H |
| W.2 | H | H | CH$_2$CH$_3$ | CF$_3$ | CH$_2$OCH$_3$ | H |
| W.3 | H | H | CH$_2$CH$_2$CH$_3$ | CF$_3$ | CH$_3$ | H |
| W.4 | H | H | CH$_2$CH$_2$CH$_3$ | CF$_2$H | CH$_3$ | H |
| W.5 | H | H | CH(CH$_3$)$_2$ | CF$_3$ | CH$_3$ | H |
| W.6 | H | H | CH(CH$_3$)$_2$ | CF$_2$H | CH$_3$ | H |
| W.7 | H | H | CH(CH$_3$)$_2$ | CFH$_2$ | CH$_3$ | H |
| W.8 | H | H | CH(CH$_3$)$_2$ | CH$_3$ | CH$_3$ | Cl |
| W.9 | H | H | CH(CH$_3$)$_2$ | CH$_3$ | CH$_2$CH$_3$ | Cl |
| W.10 | H | H | CH(CH$_3$)$_2$ | CH$_3$ | CH$_3$ | F |
| W.11 | H | H | CH(CH$_3$)$_2$ | CH$_3$ | CH$_2$CH$_3$ | F |
| W.12 | H | H | CH(CH$_3$)$_2$ | CF$_2$Cl | CH$_3$ | F |
| W.13 | H | H | CH$_2$CH$_2$CH$_2$CH$_3$ | CF$_3$ | CH$_3$ | H |
| W.14 | H | H | CH$_2$CH$_2$CH$_2$CH$_3$ | CF$_2$H | CH$_3$ | H |
| W.15 | H | H | CH$_2$CH$_2$CH$_2$CH$_3$ | CH$_3$ | CH$_3$ | F |
| W.16 | H | H | CH$_2$CH$_2$CH$_2$CH$_3$ | CH$_3$ | CH$_3$ | Cl |
| W.17 | H | H | CH$_2$CH(CH$_3$)$_2$ | CF$_3$ | CH$_3$ | H |
| W.18 | H | H | CH$_2$CH(CH$_3$)$_2$ | CF$_2$H | CH$_3$ | H |
| W.19 | H | H | CH$_2$CH(CH$_3$)$_2$ | CFH$_2$ | CH$_3$ | H |
| W.20 | H | H | CH$_2$CH(CH$_3$)$_2$ | CF$_3$ | CH$_2$OCH$_3$ | H |
| W.21 | H | H | CH$_2$CH(CH$_3$)$_2$ | CH$_3$ | CH$_3$ | F |
| W.22 | H | H | CH$_2$CH(CH$_3$)$_2$ | CH$_3$ | CH$_3$ | Cl |
| W.23 | H | H | C(CH$_3$)$_3$ | CF$_3$ | CH$_3$ | H |
| W.24 | H | H | C(CH$_3$)$_3$ | CF$_2$H | CH$_3$ | H |
| W.25 | H | H | C(CH$_3$)$_3$ | CF$_2$H | CH$_3$ | H |
| W.26 | H | H | C(CH$_3$)$_3$ | CH$_3$ | CH$_3$ | F |
| W.27 | H | H | C(CH$_3$)$_3$ | CH$_3$ | CH$_3$ | Cl |
| W.28 | H | H | C(CH$_3$)$_3$ | CF$_2$Cl | CH$_3$ | H |
| W.29 | H | H | CH$_2$CH$_2$CH$_2$CH$_2$CH$_3$ | CF$_3$ | CH$_3$ | H |
| W.30 | H | H | CH$_2$CH$_2$CH(CH$_3$)$_2$ | CF$_3$ | CH$_3$ | H |
| W.31 | H | H | CH$_2$CH$_2$CH(CH$_3$)$_2$ | CF$_2$H | CH$_3$ | H |
| W.32 | H | H | CH$_2$CH$_2$CH$_2$CH$_2$CH$_2$CH$_3$ | CF$_3$ | CH$_3$ | H |
| W.33 | H | H | cyclopropyl | CF$_3$ | CH$_3$ | H |
| W.34 | H | H | cyclopropyl | CF$_2$H | CH$_3$ | H |
| W.35 | H | H | cyclopropyl | CH$_3$ | CH$_3$ | F |
| W.36 | H | H | cyclopropyl | CH$_3$ | CH$_3$ | Cl |
| W.37 | H | H | cyclobutyl | CF$_3$ | CH$_3$ | H |
| W.38 | H | H | cyclobutyl | CF$_2$H | CH$_3$ | H |
| W.39 | H | H | cyclopentyl | CF$_3$ | CH$_3$ | H |
| W.40 | H | H | cyclopentyl | CF$_2$H | CH$_3$ | H |
| W.41 | H | H | cyclopentyl | CFH$_2$ | CH$_3$ | H |
| W.42 | H | H | cyclopentyl | CF$_2$Cl | CH$_3$ | H |
| W.43 | H | H | cyclopentyl | CH$_3$ | CH$_3$ | F |
| W.44 | H | H | cyclopentyl | CH$_3$ | CH$_3$ | Cl |
| W.45 | H | H | cyclohexyl | CF$_3$ | CH$_3$ | H |
| W.46 | H | H | cyclohexyl | CF$_2$H | CH$_3$ | H |
| W.47 | H | H | cyclohexyl | CFH$_2$ | CH$_3$ | H |
| W.48 | H | H | cyclohexyl | CF$_2$Cl | CH$_3$ | H |
| W.49 | F | F | cyclohexyl | CF$_3$ | CH$_3$ | H |
| W.50 | H | H | cyclohexyl | CH$_3$ | CH$_3$ | F |
| W.51 | H | H | cyclohexyl | CH$_3$ | CH$_3$ | Cl |
| W.52 | H | H | cycloheptyl | CF$_3$ | CH$_3$ | H |
| W.53 | H | H | cycloheptyl | CF$_3$ | CH$_2$CH$_3$ | H |
| W.54 | H | H | cycloheptyl | CF$_2$H | CH$_3$ | H |
| W.55 | H | H | cycloheptyl | CFH$_2$ | CH$_3$ | H |
| W.56 | H | H | cycloheptyl | CF$_2$Cl | CH$_3$ | F |
| W.57 | H | H | cycloheptyl | CH$_3$ | CH$_3$ | F |
| W.58 | H | H | cycloheptyl | CH$_3$ | CH$_3$ | Cl |
| W.59 | H | H | cyclooctyl | CF$_3$ | CH$_3$ | H |
| W.60 | H | H | cyclooctyl | CF$_2$H | CH$_3$ | H |
| W.61 | H | H | phenyl | CF$_3$ | CH$_3$ | H |
| W.62 | H | H | phenyl | CF$_2$H | CH$_3$ | H |
| W.63 | H | H | phenyl | CFH$_2$ | CH$_3$ | H |
| W.64 | H | H | phenyl | CH$_3$ | CH$_3$ | F |
| W.65 | H | H | phenyl | CH$_3$ | CH$_3$ | Cl |
| W.66 | H | H | 4-F—C$_6$H$_4$ | CF$_3$ | CH$_3$ | H |
| W.67 | H | H | 4-F—C$_6$H$_4$ | CF$_2$H | CH$_3$ | H |
| W.68 | H | H | 4-Cl—C$_6$H$_4$ | CF$_3$ | CH$_3$ | H |
| W.69 | H | H | 4-Cl—C$_6$H$_4$ | CF$_2$H | CH$_3$ | H |
| W.70 | H | H | 4-Br—C$_6$H$_4$ | CF$_3$ | CH$_3$ | H |
| W.71 | H | H | 4-Br—C$_6$H$_4$ | CF$_2$H | CH$_3$ | H |
| W.72 | H | H | 2-thienyl | CF$_3$ | CH$_3$ | H |
| W.73 | H | H | 3-thienyl | CF$_3$ | CH$_3$ | H |
| W.74 | H | H | 2-furyl | CF$_3$ | CH$_3$ | H |
| W.75 | H | H | 3-furyl | CF$_3$ | CH$_3$ | H |
| W.76 | H | H | α-methylcyclopropyl | CF$_3$ | CH$_3$ | H |
| W.77 | H | H | α-methylcyclopropyl | CF$_2$H | CH$_3$ | H |
| W.78 | H | H | α-methylcyclopropyl | CH$_3$ | CH$_3$ | F |
| W.79 | H | H | α-methylcyclopropyl | CH$_3$ | CH$_3$ | Cl |

TABLE X

| Compound Number | R¹ | R² | R³ | R⁴ | R⁵ |
|---|---|---|---|---|---|
| X.1 | H | H | CH$_2$CH$_3$ | CF$_3$ | CH$_3$ |
| X.2 | H | H | CH$_2$CH$_3$ | CH$_3$ | CH$_3$ |
| X.3 | H | H | CH$_2$CH$_2$CH$_3$ | CF$_3$ | CH$_3$ |
| X.4 | H | H | CH$_2$CH$_2$CH$_3$ | CH$_3$ | CH$_3$ |
| X.5 | H | H | CH(CH$_3$)$_2$ | CF$_3$ | CH$_3$ |
| X.6 | H | H | CH(CH$_3$)$_2$ | CH$_3$ | CH$_3$ |
| X.7 | H | H | CH(CH$_3$)$_2$ | CH$_2$CH$_3$ | CH$_3$ |
| X.8 | H | H | CH$_2$CH$_2$CH$_2$CH$_3$ | CF$_3$ | CH$_3$ |
| X.9 | H | H | CH$_2$CH$_2$CH$_2$CH$_3$ | CH$_3$ | CH$_3$ |
| X.10 | H | H | CH$_2$CH(CH$_3$)$_2$ | CF$_3$ | CH$_3$ |
| X.11 | H | H | CH$_2$CH(CH$_3$)$_2$ | CH$_3$ | CH$_3$ |
| X.12 | H | H | C(CH$_3$)$_3$ | CF$_3$ | CH$_3$ |
| X.13 | H | H | CH$_2$CH$_2$CH$_2$CH$_2$CH$_3$ | CF$_3$ | CH$_3$ |
| X.14 | H | H | CH$_2$CH$_2$CH$_2$CH$_2$CH$_3$ | CH$_3$ | CH$_3$ |
| X.15 | H | H | CH$_2$CH$_2$CH(CH$_3$)$_2$ | CF$_3$ | CH$_3$ |
| X.16 | H | H | CH$_2$CH$_2$CH(CH$_3$)$_2$ | CH$_3$ | CH$_3$ |
| X.17 | H | H | CH$_2$CH$_2$CH(CH$_3$)$_2$ | CH$_3$ | CH$_2$CH$_3$ |
| X.18 | H | H | CH$_2$CH$_2$CH$_2$CH$_2$CH$_2$CH$_3$ | CF$_3$ | CH$_3$ |
| X.19 | H | H | CH$_2$CH$_2$CH$_2$CH$_2$CH$_2$CH$_3$ | CH$_3$ | CH$_3$ |
| X.20 | H | H | cyclopropyl | CF$_3$ | CH$_3$ |
| X.21 | H | H | cyclopropyl | CH$_3$ | CH$_3$ |
| X.22 | H | H | cyclobutyl | CF$_3$ | CH$_3$ |
| X.23 | H | H | cyclobutyl | CH$_3$ | CH$_3$ |
| X.24 | H | H | cyclopentyl | CF$_3$ | CH$_3$ |
| X.25 | H | H | cyclopentyl | CH$_3$ | CH$_3$ |
| X.26 | H | H | cyclopentyl | CH$_3$ | CH$_3$ |
| X.27 | H | H | cyclopentyl | CH$_3$ | CH$_3$ |
| X.28 | F | F | cyclopentyl | CF$_3$ | CH$_3$ |
| X.29 | H | H | cycloheptyl | CF$_3$ | CH$_3$ |
| X.30 | H | H | cycloheptyl | CH$_3$ | CH$_3$ |
| X.31 | H | H | cyclooctyl | CF$_3$ | CH$_3$ |
| X.32 | H | H | cyclooctyl | CH$_3$ | CH$_3$ |
| X.33 | H | H | phenyl | CF$_3$ | CH$_3$ |
| X.34 | H | H | phenyl | CH$_3$ | CH$_3$ |
| X.35 | H | H | 4-F—C$_6$H$_4$ | CF$_3$ | CH$_3$ |
| X.36 | H | H | 4-F—C$_6$H$_4$ | CH$_3$ | CH$_3$ |
| X.37 | H | H | 4-Cl—C$_6$H$_4$ | CF$_3$ | CH$_3$ |
| X.38 | H | H | 4-Cl—C$_6$H$_4$ | CF$_3$ | CH$_3$ |
| X.39 | H | H | 4-Br—C$_6$H$_4$ | CF$_3$ | CH$_3$ |
| X.40 | H | H | 4-Br—C$_6$H$_4$ | CH$_3$ | CH$_3$ |
| X.41 | H | H | 2-thienyl | CF$_3$ | CH$_3$ |
| X.42 | H | H | 2-thienyl | CH$_3$ | CH$_3$ |
| X.43 | H | H | 3-thienyl | CF$_3$ | CH$_3$ |
| X.44 | H | H | 3-thienyl | CH$_3$ | CH$_3$ |
| X.45 | H | H | 2-furyl | CF$_3$ | CH$_3$ |
| X.46 | H | H | 2-furyl | CH$_3$ | CH$_3$ |
| X.47 | H | H | 3-furyl | CF$_3$ | CH$_3$ |
| X.48 | H | H | 3-furyl | CH$_3$ | CH$_3$ |
| X.49 | H | H | α-methylcyclopropyl | CF$_3$ | CH$_3$ |
| X.50 | H | H | α-methylcyclopropyl | CH$_3$ | CH$_3$ |

TABLE Y

| Compound Number | R¹ | R² | R³ | R⁴ |
|---|---|---|---|---|
| Y.1 | H | H | CH$_2$CH$_3$ | Cl |
| Y.2 | H | H | CH$_2$CH$_2$CH$_3$ | Cl |
| Y.3 | H | H | CH$_2$CH$_2$CH$_3$ | Br |

TABLE Y-continued

| Compound Number | $R^1$ | $R^2$ | $R^3$ | $R^4$ |
|---|---|---|---|---|
| Y.4 | H | H | $CH_2CH_2CH_3$ | $CF_3$ |
| Y.5 | H | H | $CH(CH_3)_2$ | Cl |
| Y.6 | H | H | $CH(CH_3)_2$ | Br |
| Y.7 | H | H | $CH(CH_3)_2$ | $CF_3$ |
| Y.8 | H | H | $CH_2CH_2CH_2CH_3$ | Cl |
| Y.9 | H | H | $CH_2CH_2CH_2CH_3$ | Br |
| Y.10 | H | H | $CH_2CH_2CH_2CH_3$ | $CF_3$ |
| Y.11 | H | H | $C(CH_3)_3$ | Cl |
| Y.12 | H | H | $CH_2CH(CH_3)_2$ | Cl |
| Y.13 | H | H | $CH_2CH(CH_3)_2$ | Br |
| Y.14 | H | H | $CH_2CH(CH_3)_2$ | $CF_3$ |
| Y.15 | H | H | $CH_2CH_2CH_2CH_2CH_3$ | Cl |
| Y.16 | H | H | $CH_2CH_2CH_2CH_2CH_3$ | Br |
| Y.17 | H | H | $CH_2CH_2CH(CH_3)_2$ | Cl |
| Y.18 | H | H | $CH_2CH_2CH(CH_3)_2$ | Br |
| Y.19 | H | H | $CH_2CH_2CH_2CH_2CH_2CH_3$ | Cl |
| Y.20 | H | H | $CH_2CH_2CH_2CH_2CH_2CH_3$ | Br |
| Y.21 | H | H | cyclopropyl | Cl |
| Y.22 | H | H | cyclopropyl | Br |
| Y.23 | H | H | cyclobutyl | Cl |
| Y.24 | H | H | cyclobutyl | Br |
| Y.25 | H | H | cyclopentyl | Cl |
| Y.26 | H | H | cyclopentyl | Br |
| Y.27 | F | F | cyclopentyl | $CF_3$ |
| Y.28 | H | H | cyclohexyl | Cl |
| Y.29 | H | H | cyclohexyl | Br |
| Y.30 | H | H | cyclohexyl | $CF_3$ |
| Y.31 | H | H | cycloheptyl | Cl |
| Y.32 | H | H | cycloheptyl | Br |
| Y.33 | H | H | cycloheptyl | $CF_3$ |
| Y.34 | H | H | cyclooctyl | Cl |
| Y.35 | H | H | phenyl | Cl |
| Y.36 | H | H | phenyl | Br |
| Y.37 | H | H | $4\text{-F—}C_6H_4$ | Cl |
| Y.38 | H | H | $4\text{-F—}C_6H_4$ | Br |
| Y.39 | H | H | $4\text{-F—}C_6H_4$ | $CF_3$ |
| Y.40 | H | H | $4\text{-Cl—}C_6H_4$ | Cl |
| Y.41 | H | H | $4\text{-Cl—}C_6H_4$ | Br |
| Y.42 | H | H | $4\text{-Cl—}C_6H_4$ | $CF_3$ |
| Y.43 | H | H | $4\text{-Br—}C_6H_4$ | Cl |
| Y.44 | H | H | 2-thienyl | Cl |
| Y.45 | H | H | 2-thienyl | Br |
| Y.46 | H | H | 3-thienyl | Cl |
| Y.47 | H | H | 3-thienyl | Cl |
| Y.48 | H | H | 2-furyl | Cl |
| Y.49 | H | H | 2-furyl | Br |
| Y.50 | H | H | 3-furyl | Cl |
| Y.51 | H | H | 3-furyl | Br |
| Y.52 | H | H | 2-pyridyl | Cl |
| Y.53 | H | H | α-methylcyclopropyl | Cl |
| Y.54 | H | H | α-methylcyclopropyl | Br |

TABLE Z

| Compound Number | $R^1$ | $R^2$ | $R^3$ | $R^4$ |
|---|---|---|---|---|
| Z.1 | H | H | $CH_2CH_3$ | $CH_3$ |
| Z.2 | H | H | $CH_2CH_2CH_3$ | $CF_3$ |
| Z.3 | H | H | $CH_2CH_2CH_3$ | $CH_3$ |
| Z.4 | H | H | $CH(CH_3)_2$ | $CF_3$ |
| Z.5 | H | H | $CH(CH_3)_2$ | $CH_3$ |
| Z.6 | H | H | $CH_2CH_2CH_2CH_3$ | $CF_3$ |
| Z.7 | H | H | $CH_2CH_2CH_2CH_3$ | $CH_3$ |
| Z.8 | H | H | $CH_2CH(CH_3)_2$ | $CF_3$ |
| Z.9 | H | H | $CH_2CH(CH_3)_2$ | $CH_3$ |
| Z.10 | H | H | $C(CH_3)_3$ | $CF_3$ |
| Z.11 | H | H | $C(CH_3)_3$ | $CH_3$ |
| Z.12 | H | H | $CH_2CH_2CH_2CH_2CH_3$ | $CF_3$ |
| Z.13 | H | H | $CH_2CH_2CH_2CH_2CH_3$ | $CH_3$ |
| Z.14 | H | H | $CH_2CH_2CH(CH_3)_2$ | $CF_3$ |
| Z.15 | H | H | $CH_2CH_2CH(CH_3)_2$ | $CH_3$ |
| Z.16 | H | H | $CH_2CH_2CH_2CH_2CH_2CH_3$ | $CF_3$ |

TABLE Z-continued

| Compound Number | $R^1$ | $R^2$ | $R^3$ | $R^4$ |
|---|---|---|---|---|
| Z.17 | H | H | $CH_2CH_2CH_2CH_2CH_2CH_3$ | $CH_3$ |
| Z.18 | H | H | cyclopropyl | $CF_3$ |
| Z.19 | H | H | cyclopropyl | $CH_3$ |
| Z.20 | H | H | cyclobutyl | $CF_3$ |
| Z.21 | H | H | cyclobutyl | $CH_3$ |
| Z.22 | H | H | cycloheptyl | $CF_3$ |
| Z.23 | H | H | cycloheptyl | $CH_3$ |
| Z.24 | H | H | cycloheptyl | $CF_3$ |
| Z.25 | H | H | cyclopentyl | $CH_3$ |
| Z.26 | H | H | cyclopentyl | $CF_3$ |
| Z.27 | F | F | cycloheptyl | $CH_3$ |
| Z.28 | H | H | cyclooctyl | $CF_3$ |
| Z.29 | H | H | phenyl | $CF_3$ |
| Z.30 | H | H | phenyl | $CH_3$ |
| Z.31 | H | H | $4\text{-F—}C_6H_4$ | $CF_3$ |
| Z.32 | H | H | $4\text{-F—}C_6H_4$ | $CH_3$ |
| Z.33 | H | H | $4\text{-Cl—}C_6H_4$ | $CF_3$ |
| Z.34 | H | H | $4\text{-Cl—}C_6H_4$ | $CH_3$ |
| Z.35 | H | H | $4\text{-Br—}C_6H_4$ | $CF_3$ |
| Z.36 | H | H | 2-thienyl | $CF_3$ |
| Z.37 | H | H | 2-thienyl | $CH_3$ |
| Z.38 | H | H | 3-thienyl | $CF_3$ |
| Z.39 | H | H | 3-thienyl | $CH_3$ |
| Z.40 | H | H | 2-furyl | $CF_3$ |
| Z.41 | H | H | 3-furyl | $CF_3$ |
| Z.42 | H | H | 2-pyridyl | $CF_3$ |
| Z.43 | H | H | 4-pyridyl | $CF_3$ |
| Z.44 | H | H | α-methylcyclopropyl | $CF_3$ |
| Z.45 | H | H | α-methylcyclopropyl | $CH_3$ |

Table 1 provides 24 compounds of formula (IIa)

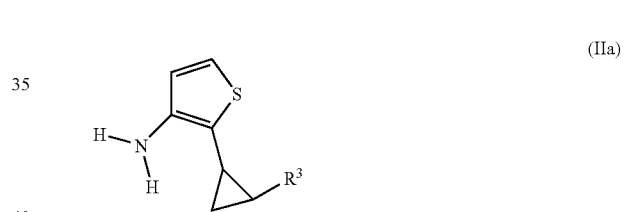

(IIa)

wherein $R^3$ is as defined in Table 1.

Table 2 provides 24 compounds of formula (IIb)

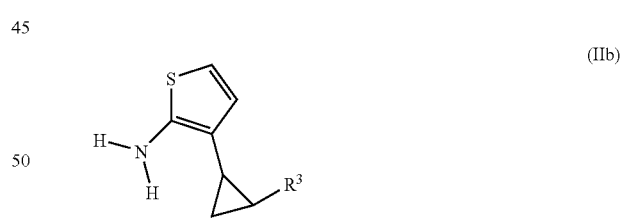

(IIb)

wherein $R^3$ is as defined in Table 2.

Table 3 provides 24 compounds of formula (IIc)

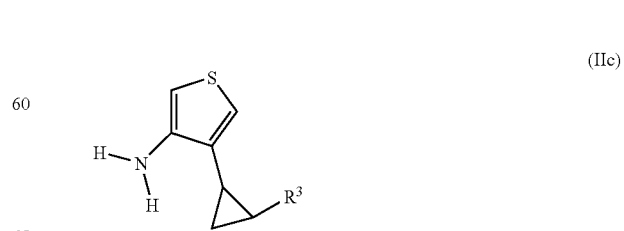

(IIc)

wherein $R^3$ is as defined in Table 3.

Table 4 provides 79 compounds of formula (Ia):

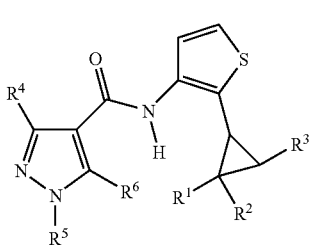

(Ia)

wherein $R^1$, $R^2$, $R^3$, $R^4$, $R^5$ and $R^6$ are as defined in Table 4.

Table 5 provides 79 compounds of formula (Ib):

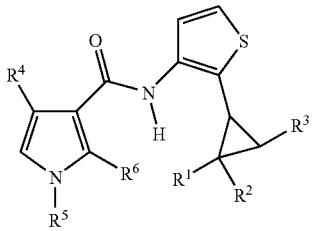

(Ib)

wherein $R^1$, $R^2$, $R^3$, $R^4$, $R^5$ and $R^6$ are as defined in Table 5.

Table 6 provides 79 compounds of formula (Ic):

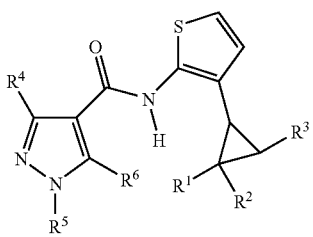

(Ic)

wherein $R^1$, $R^2$, $R^3$, $R^4$, $R^5$ and $R^6$ are as defined in Table 6.

Table 7 provides 79 compounds of formula (Id):

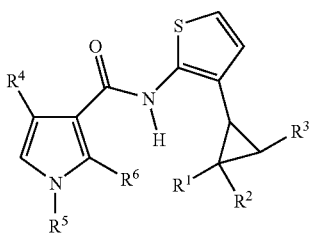

(Id)

wherein $R^1$, $R^2$, $R^3$, $R^4$, $R^5$ and $R^6$ are as defined in Table 7.

Table 8 provides 79 compounds of formula (Ie):

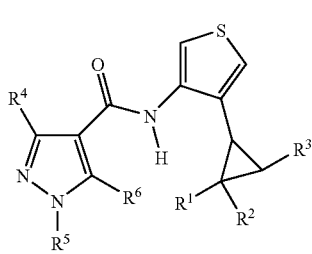

(Ie)

wherein $R^1$, $R^2$, $R^3$, $R^4$, $R^5$ and $R^6$ are as defined in Table 8.

Table 9 provides 79 compounds of formula (If):

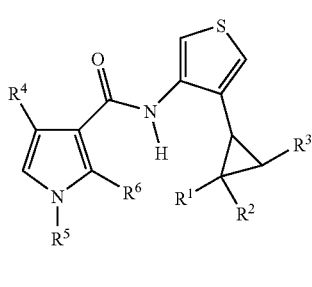

(If)

wherein $R^1$, $R^2$, $R^3$, $R^4$, $R^5$ and $R^6$ are as defined in Table 9.

Table 10 provides 50 compounds of formula (Ig):

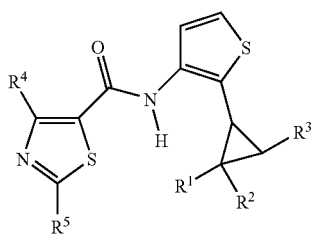

(Ig)

wherein $R^1$, $R^2$, $R^3$, $R^4$ and $R^5$ are as defined in Table 10.

Table 11 provides 50 compounds of formula (Ih):

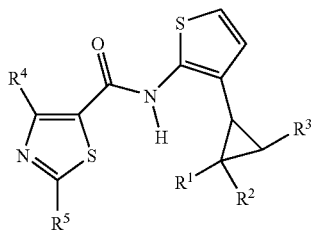

(Ih)

wherein $R^1$, $R^2$, $R^3$, $R^4$ and $R^5$ are as defined in Table 11.

Table 12 provides 50 compounds of formula (Ii):

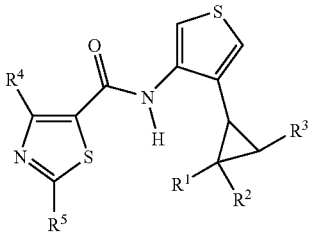
(Ii)

wherein $R^1$, $R^2$, $R^3$, $R^4$ and $R^5$ are as defined in Table 12.

Table 13 provides 54 compounds of formula (Ij):

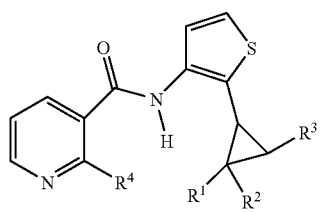
(Ij)

wherein $R^1$, $R^2$, $R^3$ and $R^4$ are as defined in Table 13.

Table 14 provides 54 compounds of formula (Ik):

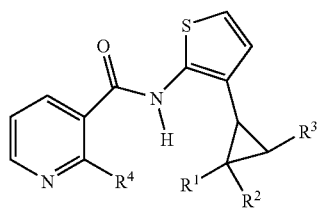
(Ik)

wherein $R^1$, $R^2$, $R^3$ and $R^4$ are as defined in Table 14.

Table 15 provides 54 compounds of formula (IL):

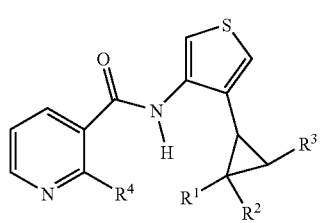
(IL)

wherein $R^1$, $R^2$, $R^3$ and $R^4$ are as defined in Table 15.

Table 16 provides 45 compounds of formula (Im):

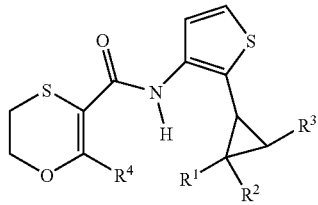
(Im)

wherein $R^1$, $R^2$, $R^3$ and $R^4$ are as defined in Table 16.

Table 17 provides 45 compounds of formula (In):

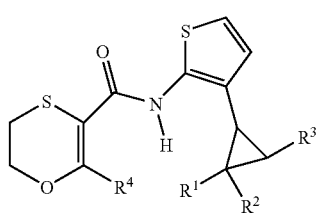
(In)

wherein $R^1$, $R^2$, $R^3$ and $R^4$ are as defined in Table 17.

Table 18 provides 45 compounds of formula (Io):

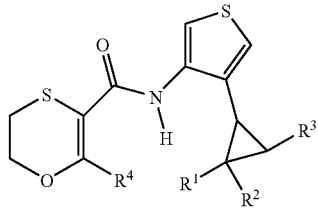
(Io)

wherein $R^1$, $R^2$, $R^3$ and $R^4$ are as defined in Table 18.

Throughout this description, temperatures are given in degrees Celsius; "NMR" means nuclear magnetic resonance spectrum; MS stands for mass spectrum; and "%" is percent by weight, unless corresponding concentrations are indicated in other units.

The following abbreviations are used throughout this description:

m.p.=melting point
s=singlet
d=doublet
t=triplet
m=multiplet
b.p.=boiling point.
br=broad
dd=doublet of doublets
q=quartet
ppm=parts per million Table 19 shows selected melting point and selected NMR data, all with CDCl$_3$ as the solvent (unless otherwise stated; if a mixture of solvents is present, this is indicated as, for example, (CDCl$_3$/d$_6$-DMSO)), (no attempt is made to list all characterising data in all cases) for compounds of Tables 1 to 18. Unless otherwise stated, the data relate to a cis/trans mixture of each compound; a compound number which ends with the letter 'c' relates only to its cis-isomer and a compound number which ends with the letter 't' relates only to its trans isomer.

TABLE 19

| Compound Number | $^1$H-NMR data: (ppm/multiplicity/number of Hs). | m.p./(° C.) |
| --- | --- | --- |
| 1.6t | 0.67/m/1H; 0.85/m/1H; 0.94/s/9H; 1.03/m/1H; 1.59/m/1H; 3.55/s(broad)/2H(NH$_2$); 6.52/d/1H; 6.85/d/1H. | oil |
| 1.10t | 0.01/m/2H; 0.27/m/2H; 0.58/m/2H; 0.73/m/1H; 0.88/m/1H; 1.31/m/1H; 3.33/s(broad)/2H(NH$_2$); 6.34/d/1H; 6.68/m/1H. | oil |
| 1.17t | 1.35-1.45/m/2H, 1.99/m/1H, 2.12/m/1H, 3.49/s(broad)/2H(NH$_2$), 6.58/d/1H, 6.93/d/1H, 7.08/d/2H, 7.25/d/2H. | oil |
| 1.18t | 1.30-1.40/m/2H, 1.97/m/1H, 2.14/m/1H, 3.5/s/2H (NH$_2$), 6.58/d/1H, 6.93/d/1H, 6.97-7.02/m/2H, 7.10-7.18/m/2H. | oil |
| 1.24t | 0.03/m/4H; 0.49/m/2H; 0.99/s/3H(Me); 1.05/m/1H; 1.23/m/1H; 3.40/s(broad)/2H(NH$_2$); 6.30/d/1H; 6.62/d/1H. | oil |
| 4.23t | | 115-116 |
| 4.24t | | 105-106 |
| 4.33 | | 103-107 |
| 4.34t | | 76-79 |
| 4.66t | | 161-162 |
| 4.67t | | 104-105 |
| 4.68t | | 147-148 |
| 4.69t | | 102-104 |
| 4.76 | | 100-108 |
| 4.77 | 0.15-0.38/m/8H(cis + trans); 0.60/m/1H(cis); 0.7-0.8/ m/2H(trans); 0.97/s/3H(cis-Me); 1.02/m/1H(cis); 1.19/s/3H(trans-Me); 1.40/m/1H(trans); 1.50/m/1H (cis); 1.62/m/1H(trans); 1.98/m/1H(cis); 3.97/s/6H (cis + trans-NMe); 6.88/t/1H(cis-CF$_2$H) 6.89/t/1H (trans-CF$_2$H); 7.0/d/1H(trans); 7.06/d/1H(cis); 7.62/d/1H(trans); 7.76/d/1H(cis); 8.03/s/1H(trans); 8.05/s/1H(cis); 8.20/s/1H(trans-NH); 8.38/s/1H(cis-NH). | resin |
| 4.78 | | 105-113 |
| 5.23t | | 90-92 |
| 5.33t | | 110-112 |
| 5.66t | | 146-148 |
| 5.68t | | 143-144 |
| 5.76 | 0.18-0.35/m/8H(cis + trans); 0.58/m/1H(cis); 0.75/m/ 2H(trans); 0.98/s/3H(cis-Me); 1.01/m/1H(cis); 1.18/ s/3H(trans-Me); 1.38/m/1H(trans); 1.47/m/1H(cis); 1.59/m/1H(trans); 1.95/m/1H(cis); 3.70/s/6H(trans + cis-Nme); 7.00/2xd/2H(trans); 7.08/d/1H(cis); 7.38/ d/1H(trans); 7.40/d/1H(cis); 7.64/d/1H(trans); 7.79/ d/1H(cis); 7.87/s/1H(trans-NH); 8.0/s/1H(cis-NH). | resin |
| 10.12t | | 71-73 |
| 10.20t | | 93-95 |
| 10.35t | | 126-128 |
| 10.37t | | 121-123 |
| 10.49 | | 85-88 |
| 13.11t | | 135-136 |
| 13.37t | | 143-145 |
| 13.40t | | 128-129 |
| 13.53 | 0.2-0.35/m/8H(cis + trans); 0.61/m/1H(cis); 0.80/m/ 2H(trans); 0.99/s/3H(cis-Me); 1.06/m/1H(cis); 1.18/ s/3H(trans-Me); 1.40/m/1H(trans); 1.49/m/1H(cis); 1.60/m/1H(trans); 1.99/m/1H(cis); 7.07/d/1H(trans), 7.11/d/1H(cis); 7.42/m/2H(cis + trans); 7.68/d/1H (trans); 7.78/d/1H(cis); 8.28/dd/1H(trans); 8.36/m/ 1H(cis); 8.40/s/1H(trans-NH); 8.53/m/2H(cis + trans); 8.68/s/1H(cis-NH). | resin |

The compounds according to formula (I) may be prepared according to the following reaction schemes.

Scheme 1

A compound of formula (IIa) [where R$^3$ is as defined above for a compound of formula (I)] may be prepared by a reaction sequence starting with a crossed-aldol condensation of 3-bromo-2-formylthiophene with a ketone of formula CH$_3$C(O)R$^3$ [where R$^3$ is as defined above for a compound of formula (I)] in the presence of NaOH or KOH in a solvent (such as water or ethanol) and usually under reflux conditions; or alternatively by reaction of 3-bromo-2-formylthiophene with an appropriate Wittig reagent under standard conditions (for example: DMSO, 20°-100° C.). The resulting α,β-unsaturated ketone of formula (IIIa) [where R³ is as defined above for a compound of formula (I)]:

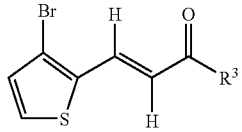

(IIIa)

may then be converted into a compound of formula (IVa) [where R³ is as defined above for a compound of formula (I)]:

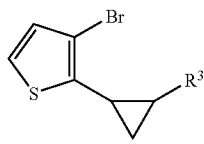

(IVa)

by reacting first with hydrazine hydrate in ethanol under reflux conditions and then heating (in the range 150 to 250° C.) in the presence of KOH (distilling off the solvent). After Pd-catalysed [tris-dibenzylidenacetondipalladium (Pd₂(dba)₃) as catalyst] reaction of a compound of formula (IVa) with benzophenonimine in the presence of a strong base [such as Na-tert-butoxide] and a ligand [such as racemic 2,2'-bis(diphenylphosphino)-1,1-binaphthyl (BINAP)] in a solvent [for example benzene, toluene or dioxane] at a temperature of 30° C. up to reflux temperature, an imine of formula (Va) is obtained [where R³ is as defined above for a compound of formula (I)]:

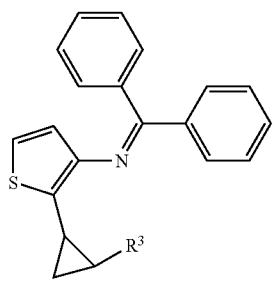

(Va)

After either a transamination reaction of a compound of formula (Va) with hydroxylamine hydrochloride in the presence of a base [preferably sodium acetate, sodium carbonate, potassium carbonate or triethylamine] preferably in a solvent [such as MeOH, EtOH or THF] and preferably at 20° C.—reflux temperature or a hydrolysis reaction of a compound of formula (Va) with an acid [preferably HCl (preferably at 0.1-12N) or sulfuric acid (preferably at 0.1%-98%)], a cis/trans-mixture of a compound of formula (IIa) is obtained, which may be further purified by distillation or flash chromatography.

The synthesis of either of the two other possible aminothiophene isomers of formulae (IIb) and (IIc) may be achieved using the methodology described above using an appropriate bromoformylthiophene as starting material.

Therefore, in a further aspect the present invention provides a process for preparing a compound of formula (II) from a compound of formula (V)

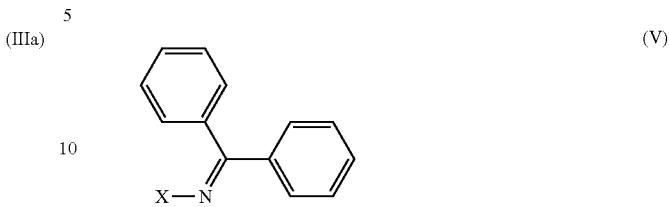

(V)

where X and R³ are as defined above for a compound of formula (I); and R¹, R², R⁷ and R⁸ are each hydrogen, comprising either a transamination reaction of a compound of formula (V) with hydroxylamine hydrochloride in the presence of a base or a hydrolysis reaction of a compound of formula (V) with an acid.

Furthermore, in an additional aspect the present invention provides a process for preparing a compound of formula (V) from a compound of formula (IV):

X—Br (IV)

where X and R³ are as defined above for a compound of formula (I); and R¹, R², R⁷ and R⁸ are each hydrogen, comprising tris-dibenzylidenacetondipalladium-catalysed reaction of a compound of formula (IV) with benzophenonimine in the presence of a strong base [preferably sodium- or potassium-tert-butanolate] and a ligand [preferably BINAP] in a solvent [preferably toluene, dioxane or THF] at a temperature between 30° C. and reflux temperature [preferably at the reflux temperature of the solvent].

Scheme 2A

The synthesis of a compound of formula (I) may be accomplished by a CuI-catalysed coupling reaction of an appropriate o-cyclopropylsubstituted bromothiophene precursor with an amide of the type HetCONH₂ [where Het is as defined above for a compound of formula (1)] in the presence of an aliphatic diamine [such as 1.2-diaminocyclohexane], in the presence of a base [such as potassium carbonate], in a solvent [such as dioxane or toluene] and at a temperature of 50° C. up to reflux temperature.

Scheme 2B

A compound of formula (I) may also be prepared by reacting a compound of formula Het-C(=O)—R* [where R* is halogen, hydroxy or $C_{1-6}$alkoxy, but preferably chloro; and Het is as defined above for a compound of formula (I)] with a compound of formula (IIa), (IIb) or (IIc) as prepared above, in the presence of a base (such as triethylamine, Hunig base, sodium bicarbonate, sodium carbonate, potassium carbonate, pyridine or quinoline, but preferably triethylamine) and in a solvent (such as diethylether, TBME, THF, dichloromethane, chloroform, DMF or NMP) for between 10 minutes and 48 hours (preferably 12 to 24 hours) and between 0° C. and reflux (preferably 20 to 25° C.). When R* is hydroxy, this is achieved with a coupling agent [such as benzotriazol-1yloxytris(dimethylamino)phosphonium hexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI)].

It will be noted that for the compounds of formula (IIa), (IIb) and (IIc) the only susbstitutuent on the cyclopropyl ring is R³; in order to prepare, via reactions analagous to scheme 2B, a compound of formula (I) where at least one of $R^1$ and $R^2$ is not hydrogen, it is necessary to prepare an appropriate precursor as described in Scheme 3.

Scheme 3

Strategies for the synthesis of o-cyclopropylsubstituted aminothiophenes where $R^1$ and $R^2$ are each, independently, hydrogen, halogen or methyl (provided that $R^1$ and $R^2$ are not both hydrogen) and $R^7$, $R^8$ are as defined above for a compound of formula (I). The starting material for this series of syntheses is 2-nitrothiophene-3-carboxaldehyde. The synthesis of this 2-nitrothiophene and related compounds is described in the literature (for example, Pharmazie 1996, 51, 386, J. Org. Chem. 1989, 54, 5094, Tetr. Letters 1987, 28, 3021 or Chem. Scr. 1980, 15, 20).

Scheme 3A:

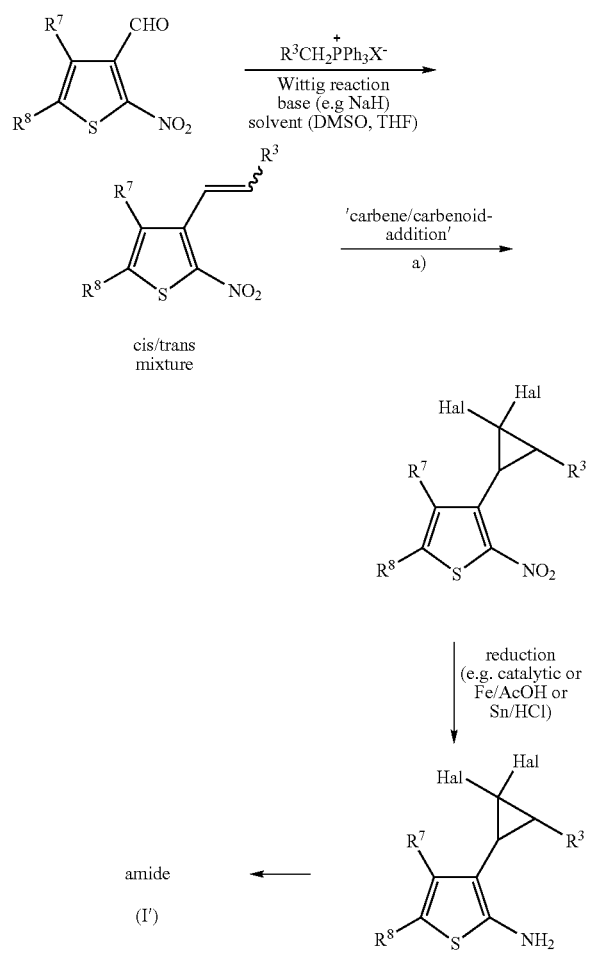

amide
(I')

Scheme 3B:

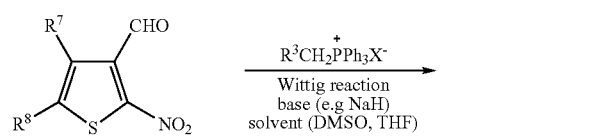

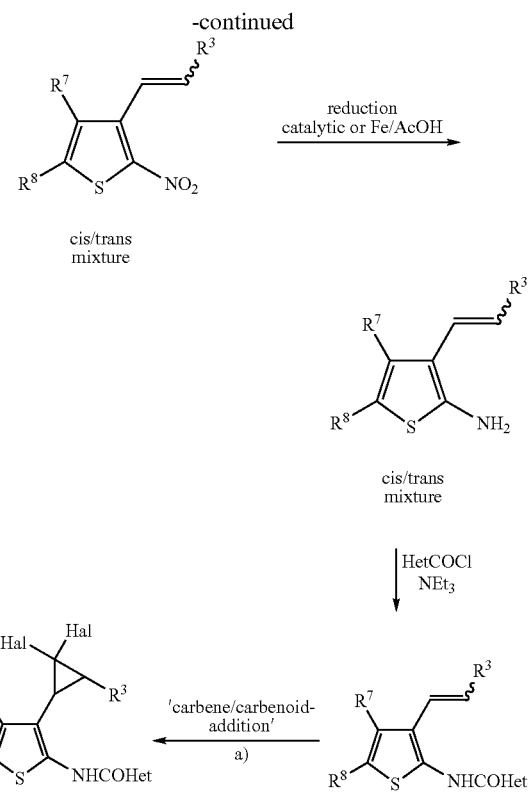

Literature for step a): Hal=Br, Cl, F a1) (Hal=F): J. Amer. Chem. Soc. 1975, 97, 344, J. Org. Chem. 1990, 55, 5420, J. Chem. Soc. Chem. Comm. 1991, 12, 826, J. Amer. Chem. Soc. 2001, 123, 8139 and Russian J. Org. Chem. 2001, 37, 207;

a2) (Hal=Cl): Chem. Ber. 1967, 100, 1858, Angew. Chemie 1974, 86, 744, J. Chem. Res. Synopses 1977, 3, 72, Synthesis 1977, 10, 682, Patent application DE 2820410, Tetrahedron Letters 1989, 30, 4697 and Synthetic Comm. 1999, 29, 4101;

a3) (Hal=Br): Tetrahedron Letters 1973, 16, 1367, Synthetic Comm. 1973, 3, 305, J. Org. Chem. 1977, 42, 1082, J. Amer. Chem. Soc. 1985, 107, 5443 and Synthetic Comm. 1988, 18, 2117.

Scheme 3C:

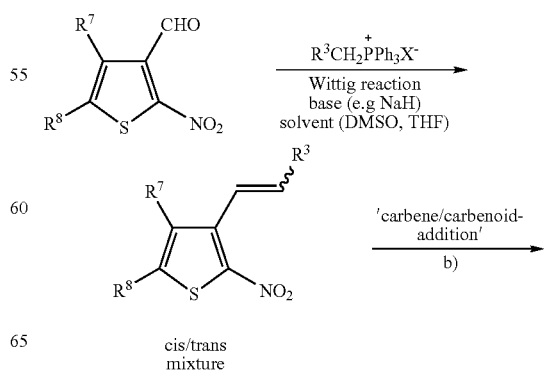

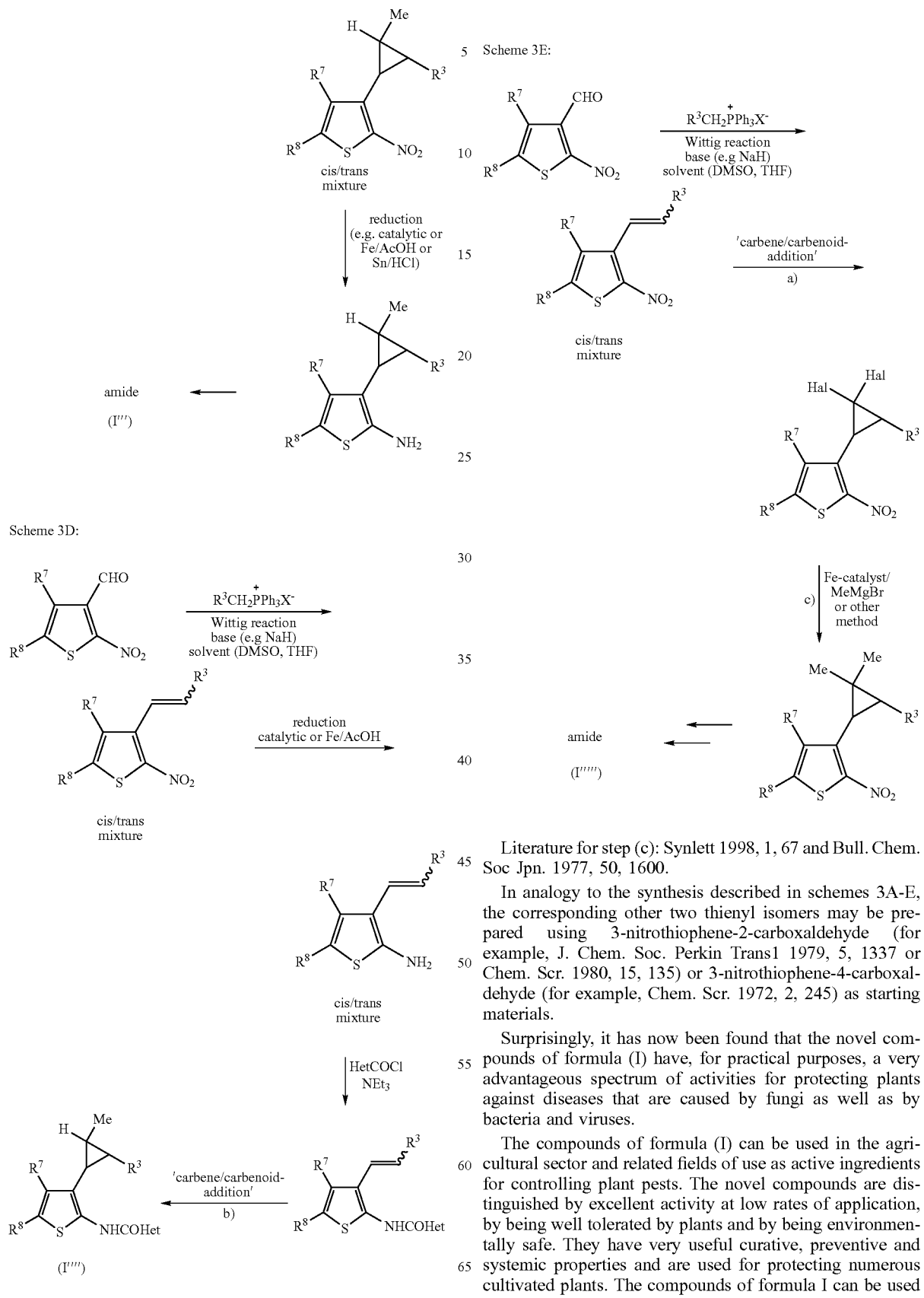

Literature for step (b): J. Org. Chem. 1991, 56, 6974 or J. Amer. Chem. Soc. 2001, 123, 139.

Literature for step (c): Synlett 1998, 1, 67 and Bull. Chem. Soc Jpn. 1977, 50, 1600.

In analogy to the synthesis described in schemes 3A-E, the corresponding other two thienyl isomers may be prepared using 3-nitrothiophene-2-carboxaldehyde (for example, J. Chem. Soc. Perkin Trans1 1979, 5, 1337 or Chem. Scr. 1980, 15, 135) or 3-nitrothiophene-4-carboxaldehyde (for example, Chem. Scr. 1972, 2, 245) as starting materials.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fuigi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imnazalil, imiben-conazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupitimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifiuzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, toldlofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of a compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (ai.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound 1.10.

In a sulfonation flask, 0.37 g (0.02 mol) of NaH (55%) was added to 50 ml of absolute DMSO. After heating at 80° C. for 90 minutes, 8.5 g (0.02 mol) cyclopropylcarbonylmethyl-triphenylphosphonium bromide was added portionwise. The resulting suspension was stirred for 45 minutes at room temperature and then a solution of 3.82 g (0.02 mol) 3-bromo-2-formylthiophene in 15 ml DMSO was added dropwise. After heating the resulting mixture for 3 hours at 50° C., the mixture was poured onto 300 ml of ice water. Extraction with ethylacetate, drying over $Na_2SO_4$ and distilling off the solvent in a water jet vacuum yielded the crude product. Purification was achieved by distillation.

Yield: 4.45 g E-3-(3-bromothiophen-2-yl)-1-cyclopropylpropenone as a yellow oil (b.p.: 95° C. at 1 Pa).

In a sulfonation flask, a mixture of 4.23 g (16 mmol) E-3-(3-bromothiophenyl-2-yl)-1-cyclopropylpropenone and 1.2 g (23.4 mmol) hyrazine hydrate in 25 ml of ethanol was heated at reflux temperature for 2 hours. Then 1.27 g (19.2 mmol) powdered potassium hydroxide (85%) was added and any excesses of hydrazine and solvent were distilled out of the flask. The remaining mixture was then heated at a temperature of 185-190° C. for 1 hour. The resulting resin was dissolved in 75 ml ethylacetate at a temperature of ca. 50° C. After washing with water, drying off the ethylacetate phase over $Na_2SO_4$ and destilling off the solvent in a water jet vacuum, the crude product was obtained. Purification was achieved by using flash-chromatography over silica gel (eluant: hexane/ethylacetate 30:1). Yield: 1.53 g of 2-bicyclopropyl-2-yl-3-bromothiophene in the form of a colourless oil (cis/trans-mixture).

A mixture of 1.37 g (5.63 mmol) of 2-bicyclopropyl-2-yl-3-bromothiophene, 1.22 g (6.75 mmol) benzophenonimine, 0.76 g (7.88 mmol) sodium tert-butoxide, 0.0021 g (0.022 mmol) tris-dibenzylidenacetondipalladium ($Pd_2(dba)_3$), 0.039 g (0.063 mmol) rac.-2,2'-bis(diphenylphosphino) 1,1-binaphthyl (BINAP) and 40 ml of absolute toluene was heated at reflux temperature under an atmosphere of nitrogene for 15 hours. After cooling, the reaction mixture was diluted with 200 ml of acetylacetate and the organic layer was washed several times with brine. After drying the organic phase ($Na_2SO_4$) and evaporation of the solvent, the crude product was obtained. The raw material was purified by flash chromatography over silica gel (eluant: hexane/diisopropylether 20:1).

Yield: 1.85 g benzhydrilidene-(2-bicyclopropyl-2-yl-thiophen-3-yl)amine in the form of a yellow oil.

In a sulfonation flask, 0.61 g (8.7 mmol) hydroxylamine hydrochloride and 0.95 g (11.62 mmol) sodiumacetate and 40 ml methanol were stirred for ca 30 minutes. Then a solution 1.66 g (4.84 mmol) benzhydrilidene-2-bicyclopropyl-2-yl-thiophen-3-ylamine in 10 ml methanol was added dropwise. Stiring at room temperature continued for 2 hours. The reaction mixture was poured onto 300 ml of ice water. Extraction with ethylacetate, drying of the organic phase ($Na_2SO_4$) and evaporation of the solvent gave the raw material. The crude product was purified by flash-chromatography over silica gel (eluant: hexane/diisopropylether 2:1). Yield: 0.78 g 2-bicyclopropyl-2-ylthiophen-3-ylamine in the form of an orange oil (cis/trans-mixture; ratio ca 1:5.5). The trans isomer was separated in pure form after an additional flash-chromatographic purification.

EXAMPLE 2

This Example illustrates the preparation of Compound 4.34.

To a solution consisting of 0.210 g (1.12 mmol) 3-difluoromethyl-1-methyl-1H-pyrazole-4-carboxylic acid, 0.185 g (1.03 mol) 2-bicyclopropyl-2-yl-thiophen-3-ylamine, 0.21 g (2.05 mmol) triethylamine and 5 ml methylenechloride was added 0.3 g (1.18 mmol) of N,N-bis(2-oxo-oxazolidinyl)phosphinic acid chloride (BOP-Cl) at 0° C. Then the ice bath was removed and the mixture was stirred at room temperature for 15 hours. Then the solvent was removed and the residue was directly purified by flash-chromatography over silica gel (eluant:hexane/ethylacetate 3:2). The resin so obtained was crystallised in cold pentane yielding the trans isomer in a purity of 97%. Yield: 0.21 g of 3-difluoromethyl-1-methyl-1H-pyrazole-4-carboxylic acid (2-bicyclo-propyl-2-yl-thiophen-3-yl)amide in the form of a white powder (trans-isomer with a purity of 97%); m.p.:76-79° C.

FORMULATION EXAMPLES FOR COMPOUNDS OF FORMULA (I)

Working procedures for preparing formulations of the compounds of formula (I), such as Emulsifiable Concentrates, Solutions, Granules, Dusts and Wettable Powders are described in WO 97/33890.

BIOLOGICAL EXAMPLES

Fungicidal Actions

Example B-1

Action Against *Puccinia recondita*/Wheat (Brownrust on Wheat)

1 week old wheat plants cv. *Arina* are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r.h. plants are kept in a greenhouse for 8 days at 20° C. and 60% r.h. The disease incidence is assessed 10 days after inoculation.

Compounds of Tables 4-12 show good activity in this test (<20% infestation). Infestation is prevented virtually completely (0-5% infestation) with each of compounds 4.23, 4.24, 4.33, 4.34, 4.77, 4.78, 5.23, 5.33, 5.76, 10.12, 10.20 and 10.49.

Example B-2

Action Against *Podosphaera leucotricha*/Apple (Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds of Tables 4, 5 and 10 show good activity in this test. Compounds 4.23, 4.24, 4.33, 4.34, 4.76, 4.77, 4.78, 5.23, 5.33, 5.76, 10.12, 10.20 and 10.49 each exhibit strong efficacy (<20% infestation).

Example B-3

Action Against *Venturia inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds of Tables 4, 5 and 10 show good activity in this test. Compounds 4.23, 4.24, 4.33, 4.34, 4.76, 4.77, 4.78, 5.23, 5.33, 5.76, 10.12, 10.20 and 10.49 each exhibit strong efficacy (<20% infestation).

Example B-4

Action Against *Erysiphe Graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r.h. in a greenhouse the disease incidence is assessed.

Compounds of Tables 4, 5 and 10 show good activity in this test. Compounds 4.23, 4.24, 4.33, 4.34, 4.76, 4.77, 4.78, 5.23, 5.33, 5.76, 10.12, 10.20 and 10.49 each exhibit strong efficacy (<20% infestation).

Example B-5

Action Against *Pyrenophora teres*/Barley (Net blotch on Barley)

1 week old barley plants cv. Express are treated with the formulated test compound (0.002% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation.

Compounds of Tables 4-18 show good activity in this test. Compounds 4.23, 4.24, 4.33, 4.34, 4.76, 4.77, 4.78, 5.23, 5.33, 5.76, 10.12, 10.20, 10.49, 13.11 and 13.53 each exhibit strong efficacy (<20% infestation).

Example B-6

Action Against *Altemaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Compounds 4.33, 4.34, 4.76, 4.77, 4.78, 5.33, 5.76, 10.20, 10.49 and 13.53 each show good activity in this test (<20% disease incidence).

Example B-7

Action Against *Uncinula necator*/Grape (Powders Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Compounds 4.33, 4.34, 4.76, 4.77, 4.78, 5.33, 5.76, 10.20 and 13.53 each show good activity in this test (<20% disease incidence).

Example B-8

Action Against *Septoria tritici*/Wheat (*Seotoria* Leaf Spot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 4.76, 4.77, 4.78, 5.76 and 10.49 each show good activity in this test (<20% disease incidence).

The invention claimed is:

1. A compound of formula (I):

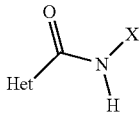
(I)

wherein
X is (X1), (X2) or (X3);

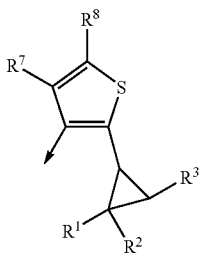
(X1)

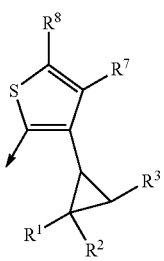
(X2)

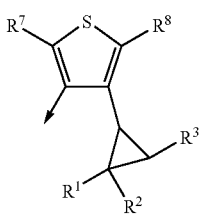
(X3)

Het is pyrrolyl, pyrazolyl, thiazolyl, or pyridinyl the ring being substituted by groups $R^4$, $R^5$ and $R^6$;
$R^1$ and $R^2$ are each, independently, hydrogen, halo or methyl;
$R^3$ is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl;
$R^4$, $R^5$ and $R^6$ are each, independently, selected from hydrogen, halo, cyano, nitro, $C_{1-4}$ alkyl, $C_{1-4}$ haloalkyl, $C_{1-4}$ alkoxy($C_{1-4}$)alkylene and $C_{1-4}$ haloalkoxy($C_{1-4}$)alkylene, provided that at least one of $R^4$, $R^5$ and $R^6$ is not hydrogen; and
$R^7$ and $R^8$ are each, independently, hydrogen, halogen, $C_{1-4}$ alkyl or $C_{1-4}$ haloalkyl.

2. A compound of formula (I) as claimed in claim 1, where $R^1$ and $R^2$ are, independently, hydrogen or fluoro.

3. A compound of formula (I) as claimed in claim 1, where $R^3$ is $C_{2-6}$ alkyl, optionally substituted $C_{3-8}$ cycloalkyl, phenyl, thienyl or furyl.

4. A compound of formula (I) as claimed in claim 1, where $R^4$, $R^5$ and $R^6$ are, independently, selected from hydrogen, halogen, $C_{1-4}$ alkyl, $C_{1-4}$ haloalkyl and $C_{1-4}$ alkoxy($C_{1-4}$) alkylene, provided that at least one of $R^4$, $R^5$ and $R^6$ is not hydrogen.

5. A compound formula (ll):

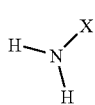
(II)

where X and $R^3$ are as defined in claim 1; and $R^1$, $R^2$, $R^7$ and $R^8$ are each hydrogen.

6. A process for preparing a compound of formula (II) as claimed in claim 5 from a compound of formula (V):

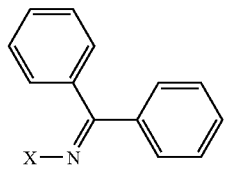
(V)

where X, $R^1$, $R^2$, $R^3$, $R^7$ and $R^8$ are as defined in claim 5, comprising either a transamination reaction of a compound of formula (V) with hydroxylamine hydrochloride in the presence of a base or a hydrolysis reaction of a compound of formula (V) with an acid.

7. A process for preparing a compound of formula (V) as defined in claim 6 from a compound of formula (IV):

X—Br (IV)

where X, $R^1$, $R^2$, $R^3$, $R^7$ and $R^8$ are as defined in claim 5, comprising tris-dibenzylideneacetondipalladium-catalysed reaction of a compound of formula (IV) with benzophenonimine in the presence of a strong base and a ligand in a solvent at a temperature between 30° C. and reflux temperature.

8. A composition for controlling microorganisms and preventing attack and infestation of plants therewith, wherein the active ingredient is a compound of formula (I) as claimed in claim 1 together with a suitable carrier.

9. A method of controlling or preventing infestation of cultivated plants by phytopathogenic microorganisms by application of a compound of formula (I) as claimed in claim 1 to plants, to parts thereof or the locus thereof.

* * * * *